United States Patent [19]

Temple, Jr. et al.

[11] 4,411,901

[45] Oct. 25, 1983

[54] BENZISOTHIAZOLE AND BENZISOXAZOLE PIPERAZINE DERIVATIVES

[75] Inventors: Davis L. Temple, Jr., Evansville; Joseph P. Yevich, Newburgh, both of Ind.

[73] Assignee: Mead Johnson & Company, Evansville, Ind.

[21] Appl. No.: 333,830

[22] Filed: Dec. 23, 1981

[51] Int. Cl.³ ............... C07D 401/00; C07D 413/00; A61K 31/41
[52] U.S. Cl. .................... 424/250; 544/360; 544/364; 544/230; 544/368; 544/373
[58] Field of Search ............... 544/230, 364, 360; 424/250

[56] References Cited

U.S. PATENT DOCUMENTS

| 3,367,936 | 2/1968 | Koppe et al. | 544/360 |
| 3,398,151 | 8/1968 | Wu et al. | 544/230 |
| 3,717,634 | 2/1973 | Wu et al. | 544/230 |
| 4,182,763 | 1/1980 | Casten et al. | 424/250 |

FOREIGN PATENT DOCUMENTS 2023594  1/1980  United Kingdom ............... 544/360

OTHER PUBLICATIONS

Wu et al., J. Med. Chem., 12, 876–881, (1969) (2/7).
Rojsner et al., Coll. Czech. Chem. Comm., 40(4), 1218–1230, (1975).
Jones et al., J. Chem. Soc., London, 91–92 (1946).
Benica et al., J. Am. Pharm. Assoc., 451–456 (1950).
Wu et al., J. Med. Chem. 15, 477–479, (1972).

*Primary Examiner*—Donald G. Daus
*Assistant Examiner*—S. A. Gibson
*Attorney, Agent, or Firm*—Robert H. Uloth; Richard P. Ryan

[57] ABSTRACT

Disubstituted N,N-piperazinyl derivatives are disclosed wherein one substituent is benzisothiazol-3-yl or benzisoxazol-3-yl and the other is alkylene attached to heterocycles such as azaspiro[4.5]decanedione, dialkylglutarimide, thiazolidinedione and spirocyclopentylthiazolidinedione or butyrophenone-like groups. The compounds have psychotropic properties and 8-[4-[4-(1,2-benzisothiazol-3-yl)-1-piperazinyl]butyl]-8-azaspiror[4.5]decane-7,9-dione is a typical embodiment having selective antipsychotic activity.

12 Claims, No Drawings

4,411,901

BENZISOTHIAZOLE AND BENZISOXAZOLE PIPERAZINE DERIVATIVES

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein one substituent is 1,2-benzoisothiazol-3-yl or 1,2-benzisoxazol-2-yl and the other is a heterocycle (attached via an alkylene chain) or a butyrophenone-like (and corresponding carbinol) radical as depicted:

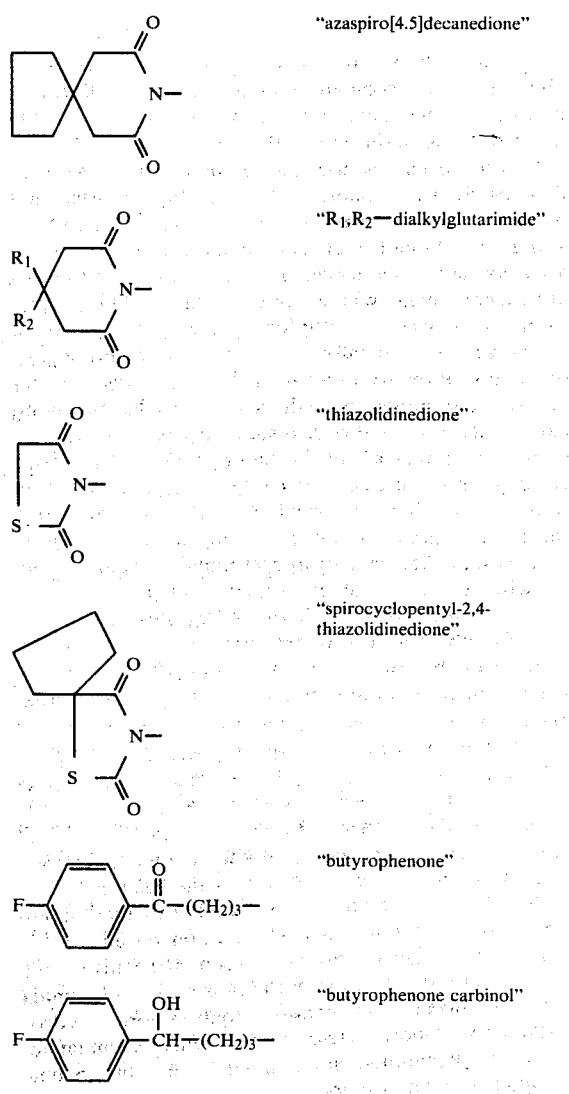

Wu, U.S. Pat. No. 3,398,151, Wu, et al., U.S. Pat. No. 3,717,634 and, respectively, corresponding Wu, et al., publications—J. Med. Chem., 12, 876-881 (1969), 15, 447-479 (1972)—variously describe azaspiro[4.5]decanedione and dialkylglutarimide psychotropic compounds resembling formula (1)

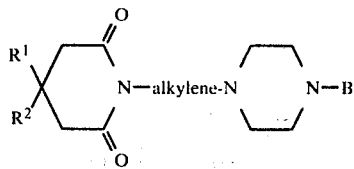

wherein $R^1$ and $R^2$ are alkyl or joined to form —$(CH_2)_4$— or —$(CH_2)_5$— and B inter alia represents phenyl plus various heterocyclies (all with optional substituents):

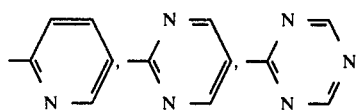

Casten, et al., U.S. Pat. No. 4,182,763 concerns the anxiolytic use of compound (4) which is referred to in the biological literature as buspirone.

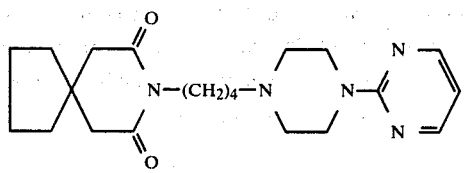

Benica, et al., J. Am. Pharmaceutical Association, 451-456 (1950) describes 3,3-dialkylglutarimides wherein $R^1$ is $C_{1-4}$ alkyl and $R^2$ is hydrogen or $C_{1-4}$ alkyl as shown in formula (3) and states the compounds lacked significant physiological activity.

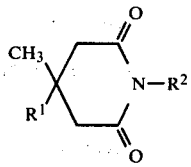

Thiazolidinediones are known to the art. For example, Jones, et al., J. Chem. Soc., London, 91-92 (1946) refer to 5,5-dialkyl-2,4-thiazolidinedione barbituric acid analogs and disclose that a 5-spirocyclohexyl-2,4-thiazolidinedione (4) produced narcosis and analgesia in mice.

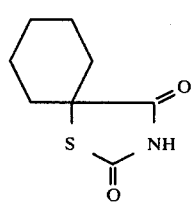

Various types of 1,4-substituted piperazine derivatives are also known to the art as illustrated in the following references.

Great Britain No. 2,023,594A discloses 1-(R-alkyl)-4-(3-trifluoromethylthiophenyl)piperazines useful for treating anxiety and depression having general formula (5)

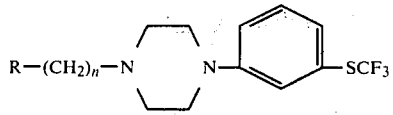

wherein n is 1–3 and R inter alia represents heterocycles such as

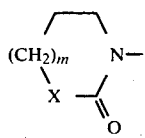

wherein m is 0 or 1 and X is a —S—, —O—, imino, alkyl-imino or methylene.

Rojsner, et al., Collect. Czech. Chem. Commun., 40(4) 1218-1230 (1975) inter alia describe butyrophenone derivatives of formula (6) as part of a psychotropic structure-activity-relationship study.

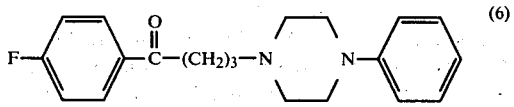

None of the aforementioned references disclose or suggest the 1,2-benzisothiazole or 1,2-benzisoxazole piperazine derivatives of the instant invention.

SUMMARY AND DETAILED DESCRIPTION OF THE INVENTION

In its broadest aspect, the present invention is concerned with piperazinyl derivatives having neuroleptic (antipsychotic) properties characterized by a compound of Formula (I)

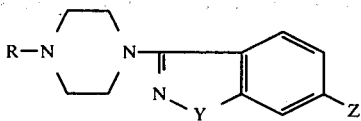

wherein R represents the radical

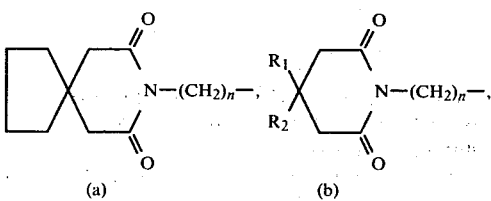

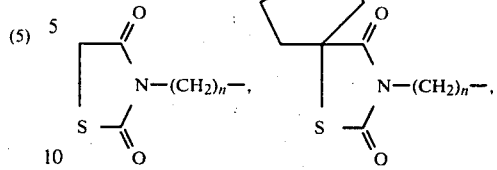

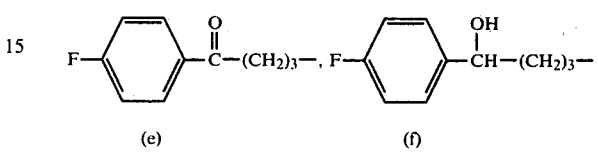

in which n is 3 or 4, $R_1$ and $R_2$ are independently lower alkyl of 1 to 4 carbon atoms, Y is oxygen or sulfur, Z is hydrogen or halogen, or a pharmaceutically acceptable non-toxic acid addition salt thereof.

It is to be understood that, as used herein, halogen denotes fluorine, iodine and preferably chlorine and bromine with the term "lower alkyl" referring to both straight and branched chain carbon radicals of from 1 to 4 carbon atoms inclusive. Illustrative of these radicals are carbon chains which can be methyl, ethyl, propyl, isopropyl, 1-butyl, 1-methylpropyl and 2-methylpropyl.

The pharmaceutically acceptable acid addition salts of the invention are those in which the anion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid preferably by contact in solution employing an excess of commonly used inert solvents such as water, ether, benzene, ethanol, ethyl acetate and preferably acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, mandelic, phosphoric, nitric, mucic, isethionic, palmitic, heptanoic, and others.

The compounds of Formula I wherein R is radical "a, b, c and d" of the instant invention are obtained by procedures involving alkylation of piperazinyl or "imide" intermediates analogous to methods described by Wu, et al., patents supra., incorporated herein in entirety by reference. Such methods are illustrated below for preparation of a preferred Formula I compound (R=a, n=4, Y=S, Z=H), 8-[4-[4-(1,2-benzisothiazol- 3-yl)-1-piperazinyl]butyl]-8-azaspiro[4.5]decane-7,9-dione (Ia₁):

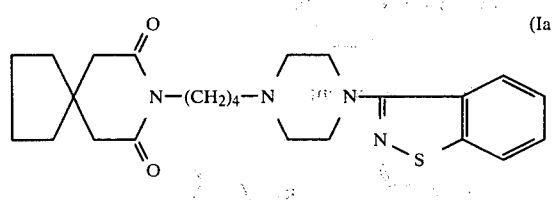

Method A

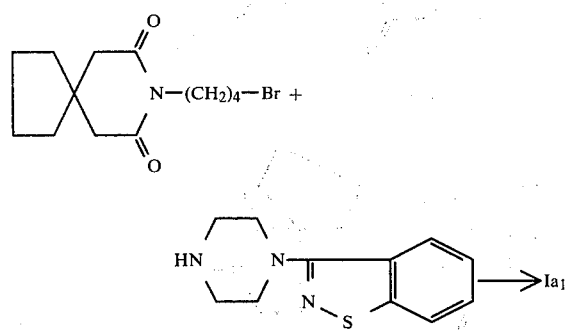

Method B

Type 1

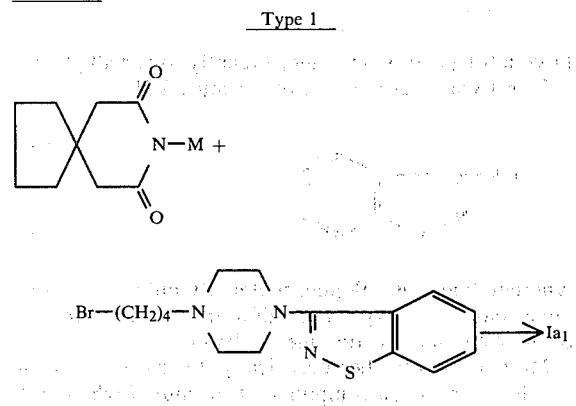

Type 2

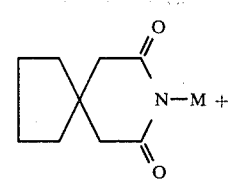

Method C

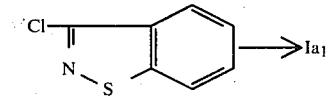

Method D

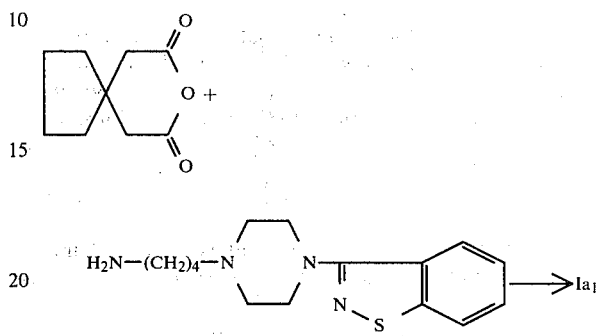

In the foregoing reaction schemes, "M" denotes an alkali metal salt and the specific halogen recited is given only by way of example with other members of the halogen class (e.g., chlorine, bromine, iodine) operable as well as suitable displacement groups such as sulfate, phosphate, tosylate, mesylate and the like.

Method A is further generically described as a process for preparing a compound of Formula I wherein R is the radical "a, b, c or d" as previously defined therefor which comprises reacting an imidoyl compound of Formula II Imid-A (II)

wherein "A" is —(CH₂)$_n$—X in which "n" is 3 or 4 and "X" is the acid residue of a reactive ester grouping such as chloride, bromide, iodide, fluoride, sulfate, phosphate, tosylate or mesylate, and "Imid" represents

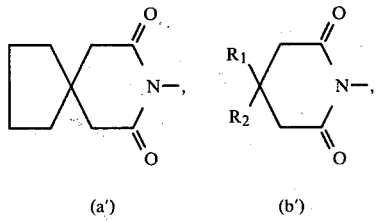

(a') (b')

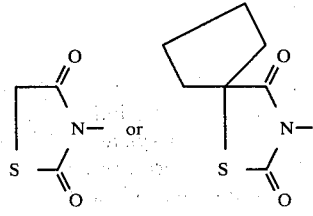

(c') (d')

in which R₁ and R₂ are independently lower alkyl with a compound of Formula III

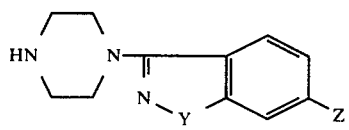

(III)

wherein "Y" is oxygen or sulfur and "Z" is hydrogen or halogen; in a reaction inert solvent.

Method B is further generically described as a process for preparing a compound of Formula I wherein R is the radical "a, b, c or d" as previously defined which comprises reacting an imidoyl compound of Formula IV Imid-M    (IV)

wherein "M" is an alkali metal salt such as sodium, potassium or lithium and "Imid" represents

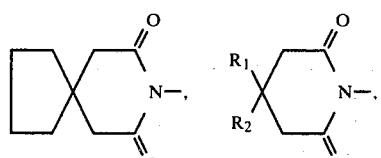

(a')    (b')

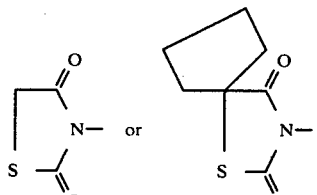

(c')    (d')

in which $R_1$ and $R_2$ are independently lower alkyl with a compound of Formula V or V'

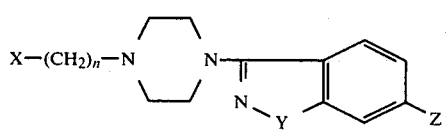

(V)

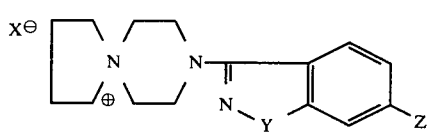

(V')

wherein "X" is the acid residue of a reactive ester grouping such as chloride, bromide, iodide, fluoride, sulfate, phosphate, tosylate, or mesylate, and in Formula V' is preferably bromine, chlorine or iodine, "n" is 3 or 4, "Y" is oxygen or sulfur, and "Z" is hydrogen or halogen in a reaction inert solvent.

Method C is further generically described as a process for preparing a compound of Formula I wherein R is the radical "a, b, c and d" as previously defined which comprises reacting a compound of Formula VI

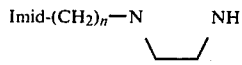

(VI)

wherein "Imid" represents

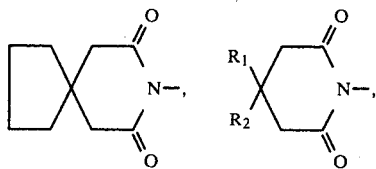

(a')    (b')

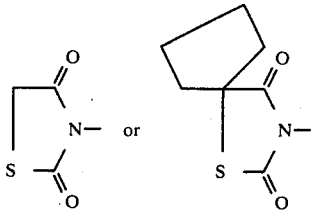

(c')    (d')

in which $R_1$ and $R_2$ are independently lower alkyl, "n" is 3 or 4 with a compound of Formula VII

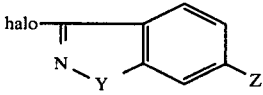

(VII)

wherein "halo" is halogen, preferably chlorine or bromine, and "Y" is oxygen or sulfur and "Z" is hydrogen or halogen; in a reaction inert solvent.

Method D is further generically described as a process for preparing a compound of Formula I wherein R is the radical "a, b, c or d" as previously defined which comprises reacting an anhydride of Formula VIII(a, b, c, or d)

(VIIIa)    (VIIIb)

(VIIIc)    (VIIId)

in which $R_1$ and $R_2$ are independently lower alkyl with a compound of Formula IX

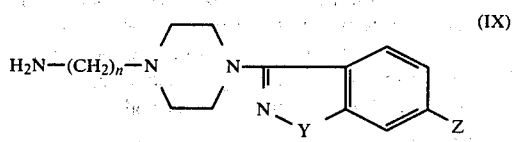 (IX)

wherein "n" is 3 or 4, "Y" is oxygen or sulfur and "Z" is hydrogen or halogen; in a reaction inert solvent.

The foregoing generic embodiments of Methods A, B and C constitute a unitary process for preparing compounds of Formula I wherein R is the radical "a, b, c or d" as previously described which comprises alkylating a compound of Formula III, IV or VI with an appropriate alkylating intermediate of Formula II, V, V' or VII in a reaction inert solvent.

Methods A and C are conventionally carried out under reaction conditions employed in preparing tertiary amines by alkylating secondary amines. Thus, the compounds of Formula I wherein R is radical "a, b, c and d" are obtained by reacting appropriate intermediates in an inert reaction medium at temperatures of from about 50° to about 200° C. in the presence of a base suitable for use as an acid binding agent. Operable inorganic and organic acid binding bases include tertiary amines, alkali and alkaline earth metal carbonates, bicarbonates, or hydrides with sodium carbonate and potassium carbonate particularly preferred. As referred to throughout the specification, the term "inert reaction medium" refers to any protic or aprotic solvent or diluent which does not enter into the reaction to any substantial degree. In this regard, acetonitrile is a particularly preferred solvent with the reaction conveniently carried out at reflux temperature. Satisfactory yields of the present compounds are obtained with reaction periods ranging from about 2–24 hours. Formula (I) products may be purified by crystallization techniques from standard solvent media such as acetonitrile, isopropanol, methanol, ethanol and the like and by other conventional methods such as chromatography employing a silica gel column with mixtures of chloroform and alkanols such as methanol and ethanol as eluant.

Method B illustrates a modification of the unitary process of the instant invention for preparation of Formula I wherein R is radical "a, b, c and d" compounds in which an alkali metal salt of an imide intermediate of Formula IV is alkylated. Standard laboratory procedures are employed in carrying out this reaction such as those described for the alkylation step of the Gabriel synthesis—S. Gabriel, Ber. 20, 2224 (1887). In the present case, for instance, the reactants are combined in an inert reaction medium at temperatures ranging from 50° C. to 200° C. Toluene and xylene are particularly preferred solvents for carrying out the reaction but other solvents which do not adversely affect the reaction or reactants can be employed. In this regard, solvents such as dioxane, benzene, dimethylformamide, acetone, acetonitrile, n-butanol and the like are operable. In general, the alkali metal salts (IV) are prepared by treating the corresponding imide precursor with an alkali hydride such as sodium hydride, an alkali alcoholate such as sodium ethoxide, an alkali amide such as sodium amide, an alkali base such as sodium hydroxide, potassium hydroxide, an alkali carbonate such as sodium carbonate or potassium carbonate in a suitable solvent. It is not necessary to pre-form the Formula IV alkali metal salts and the imide precursor and piperazinyl alkylating agent (V or V') can be conveniently combined in an inert reaction medium in the presence of a base, preferably sodium or potassium carbonate.

Compounds of Formula I wherein R is the radical "e or f" are obtained by a process involving alkylation of a piperazinyl intermediate of Formula III

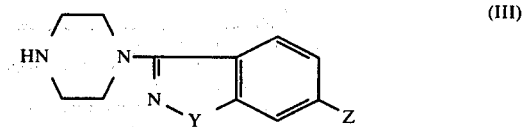 (III)

wherein "Y" is oxygen or sulfur and "Z" is hydrogen or halogen with a compound of Formula X

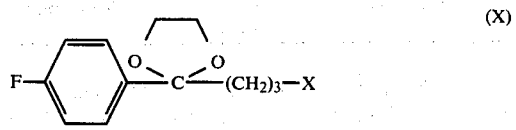 (X)

wherein "X" is as defined above and most preferably chlorine or bromine in a reaction inert solvent to provide the compounds of Formula Ie

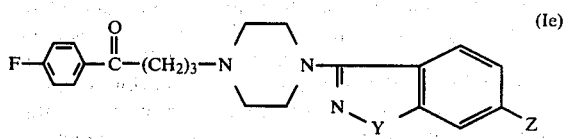 (Ie)

and thereafter reducing (Ie) to afford the corresponding compounds of Formula If

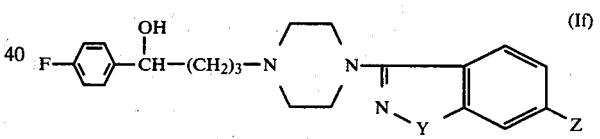 (If)

Piperazinyl benzisothiazole and benzisoxazole intermediates of Formula (III) are obtained by reaction of 3-chloro-6-Z-1,2-benzisothiazole or 3-chloro-6-Z-1,2-benzisoxazole with excess piperazine at elevated temperature. For example, 3-chloro-1,2-benzisothiazole starting material is prepared by treating 1,2-benzisothiazol-3(2H)one with phosphorous pentachloride at 100°–140° C. for 4 hours. A similar conversion of 1,2-benzisoxazol-3-one to 3-chloro-1,2-benzisoxazole is carried out with phosphorus oxychloride/triethylamine according to the procedure of H. Boshagen, Ber. 100, 3326 (1967).

The compounds of the instant invention are useful pharmacological agents with psychotropic properties. In this regard, they exhibit selective central nervous system activity at non-toxic doses and are of particular interest as neuroleptic (antipsychotic) agents. As with other known antipsychotics, the compounds of Formula (I) evoke certain responses in standard in vivo and in vitro pharmacological test systems which are known to correlate well with relief of anxiety and symptoms of acute and chronic psychosis in man. The following are illustrative of such conventional in vivo test systems used to classify and differentiate a psychotropic agent from a nonspecific CNS depressant and determine potential side-effect liabilities (e.g., cataleptic activity). Regarding the latter, antipsychotic agents as a class are known to produce sedation and extrapyramidyl reactions such as acute torsion dystonia, akathiasia, parkinsonism, tardive dyskinesia and autonomic nervous system effects.

| Behavioral Test | Reference |
|---|---|
| Suppression of conditioned avoidance response (CAR) | Albert, Pharmacologist, 4, 152 (1962); Wu et al., J. Med. Chem., 12, 876-881 (1969). |
| Catalepsy | Costall, et al., Psychopharmacologia, 34, 233-241 (1974); Berkson, J. Amer. Statist. Assoc., 48, 565-599 (1953). |
| Fighting Mouse | Tedeschi, et al., J. Pharmacol. Expt. Therap., 125, 28 (1959). |
| Rotarod | Kinnard, et al., J. Pharmacol. Expt. Therap., 121, 354 (1957). |
| Apomorphine Stereotypy | Jannsen, et al., Arzneimittel. Forsch., 17, 841 (1966). |

As further indication of the psychotropic activity and specificity of the instant compounds, state of the art in vitro central nervous system receptor binding methodology can be employed. Certain compounds (commonly referred to as ligands) have been identified which preferentially bind to specific high affinity sites in brain tissue dealing with psychotropic activity or potential for side effects. Inhibition of radiolabeled ligand binding to such specific high affinity sites is considered a measure of a compound's ability to affect corresponding central nervous system function or cause side effects in vivo. This principal is employed in the following assays which are given by way of example.

| Receptor Binding Assay | Reference |
|---|---|
| Dopamine | Burt, et al., Molec. Pharmacol., 12, 800 (1976); Science, 196, 326 (1977); Creese, et al, Science, 192, 481 (1976). |
| Cholinergic | Yamamura, et al., Proc. Natn. Acad. Sci. USA 71 1725 (1974). |
| Alpha-receptor | Crews, et al., Science 202: 322 (1978); Rosenblatt, et al., Brain Res. 160: 186 (1979); U'Prichard, et al., Science 199: 197 (1978); U'Prichard, et al., Molec. Pharmacol. 13: 454 (1977). |
| Serotonin Type 2 | Peroutka and Snyder, Molec. Pharmacol. 16: 687 (1979). |

According to the pharmacological profile established by the aforementioned tests, the instant compounds of Formula (I) have promising antipsychotic potential in that they are relatively potent in the CAR test having oral ED$_{50}$ values <100 mg/kg body weight and IC$_{50}$'s of <1000 nanomolar in the $^3$H spiperone dopamine receptor binding assay. Activity in the CAR test and spiperone assay is considered predictive of antipsychotic potential in man. Regarding selective antipsychotic activity, preferred compounds of the invention have significant dopamine receptor binding activity and suppress rat CAR below cataleptic doses.

A particularly preferred compound in this regard is 8-[4-[4-(1,2-benzoisothiazol-3-yl)-1-piperazinyl]butyl]-8-azaspiro-[4.5]decane-7,9-dione which exhibits relatively weak cataleptogenic activity in the rat at approximately 8 times the CAR dose suggesting minimal potential for extrapyramidal side effects.

As previously mentioned, the instant compounds have psychotropic properties particularly suited to their use as a neuroleptic (antipsychotic) agent. Thus, another aspect of the instant invention concerns a process for ameliorating a psychotic state in a mammal in need of such treatment which comprises systemic administration to said mammal an effective dose of from about 0.01 to 40 mg/kg body weight of a Formula (I) compound or a pharmaceutically acceptable acid addition salt thereof.

The term systemic administration as used herein refers to oral, rectal, and parenteral (i.e., intramuscular, intravenous, and subcutaneous) routes. Generally, it will be found that when a compound of the present invention is administered orally which is the preferred route, a larger quantity of the active agent is required to produce the same effect as a smaller quantity given parenterally. In accordance with good clinical practice, it is preferred to administer the instant compounds at a concentration level that will produce effective neuroleptic (antipsychotic) effects without causing any harmful or untoward side effects.

Therapeutically, the instant compounds are generally given as pharmaceutical compositions comprised of an effective antipsychotic amount of a compound of Formula I or a pharmaceutically acceptable acid addition salt thereof and a pharmaceutically acceptable carrier. Pharmaceutical compositions which provide from about 1 to 500 mg. of the active ingredient per unit dose are preferred and are conventionally prepared as tablets, lozenges, capsules, powders, aqueous or oily suspensions, syrups, elixirs and aqueous solutions.

Preferred oral compositions are in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propylene glycol, and polyethyleneglycols or mixtures thereof. The polyethyleneglycols consist of a mixture of non-volatile, normally liquid, polyethyleneglycols which are soluble in both water and organic liquids and which have molecular weights of from about 200 to 1500.

The following non-limiting examples serve to illustrate preparation of specific compounds of the instant inventions.

EXAMPLE 1

3-(1-Piperazinyl)-1,2-benzisothiazole

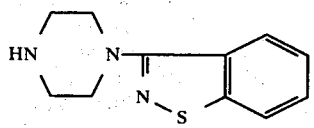

A mixture of 3-chloro-1,2-benzisothiazole (37.8 g., 0.235 mole) and piperazine (304.2 g., 3.53 mole) is heated under an argon atmosphere for a period of 20 hr. at 120° C. in a closed reactor. The reaction mixture is dissolved in 2 liters of water and the aqueous solution repeatedly extracted with methylene chloride. Extracts are combined, dried over magnesium sulfate and concentrated in vacuo. Residual material is taken up in ether, filtered and concentrated in vacuo to afford 24.4 g. (47%) of 3-(1-piperazinyl)-1,2-benzisothiazole free base as a viscous oil.

A sample of the free base converted to the hydrochloride salt in ether with ethanolic hydrogen chloride and crytallized from methanol-ethanol affords analytically pure 3-(1-piperazinyl)-1,2-benzisothiazole hydrochloride, m.p. 280° C. (dec.).

Anal. Calcd. for $C_{11}H_{13}N_3S.HCl$: C, 51.66; H, 5.52; N, 16.43. Found: C, 51.34; H, 5.46; N, 16.16.

EXAMPLE 2

3-(1-Piperazinyl)-1,2-benzisoxazole

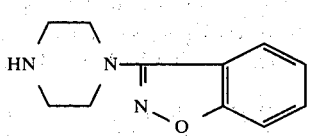

A mixture of 3-chloro-1,2-benzisoxazole (19.6 g., 0.128 mole) and piperazine (110 g., 1.28 mole) is heated for a period of 20 hr. at 120° C. in a closed reactor. The reaction mixture is diluted with water and the aqueous mixture repeatedly extracted with methylene chloride. Extracts are combined, dried over magnesium sulfate and concentrated in vacuo to afford 21.2 g. (82% yield) of 3-(1-piperazinyl)-1,2-benzidoxazole free base.

A sample of the free base converted to the hydrochloride salt and crystallized from methanol-ethanol affords analytically pure 3-(1-piperazinyl)-1,2-benzisoxaole hydrochloride, m.p. 326° C. (dec.).

Anal. Calcd. for $C_{11}H_{13}N_3O.HCl$: C, 55.12; H, 5.89; N, 17.54. Found: C, 55.25; H, 5.82; N, 17.53.

EXAMPLE 3

8-[4-[4-(1,2-Benzisothiazol-3-yl)-1-piperazinyl]butyl]-8-azaspiro[4.5]decane-7,9-dione

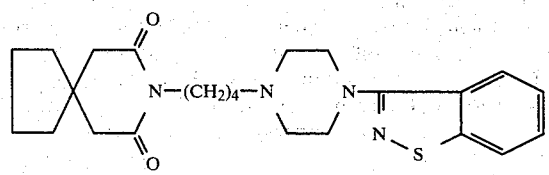

Method A. A mixture of 3-(1-piperazinyl)-1,2-benzisothiazole (24.3 g., 0.11 mole) and 8-(4-bromobutyl)-8-azaspiro-[4.5]decane-7,9-dione (33.5 g., 0.11 mole), anhydrous potassium carbonate (32.4 g., 0.23 mole) and potassium iodide (3.9 g., 0.023 mole) in 1 liter of acetonitrile is stirred and heated under reflux for a period of 20 hr. The reaction mixture is filtered, concentrated in vacuo and residual material taken up in 350 ml. of chloroform which is filtered and concentrated in vacuo. The residue is triturated with ether, refrigerated and resulting solid collected. This material crystallized from acetonitrile (employing activated charcoal affords a first crop 25.1 g, m.p. 120°-124° C. and a second crop, 6.0 g, m.p. 123°-126° C. for a total yield of 31.1 g. (64% yield) of the free base form of the title compound. Crystallization from acetonitrile affords analytically pure 8-[4-[4-(1,2-benzoisothiazol-3-yl)-1-piperazinyl]butyl]-8-azaspiro[4.5]decane-7,9-dione, m.p. 124°-126° C.

Anal. Calcd. for $C_{24}H_{32}N_4O_2S$: C, 65.42; H, 7.32; N, 12.72. Found: C, 65.45; H, 7.31; N, 12.75.

NMR (CDCL$_3$): 1.60 (12H, m); 2.57 (4H, s); 2.62 (6H, m); 3.54 (4H, m); 3.79 (2H, m); 7.34 (2H, m); 7.81 (2H, m).

Ethanolic hydrogen chloride (12.3 ml. of 5.7 N) is added to a suspension of the free base (31 g) in hot isopropanol. The resulting solution is cooled and the precipitate formed collected and dried in vacuo at 80° C. to provide 29.6 g. of 8-[4-[4-(1,2-benzisothiazol-3-yl)-1-piperazinyl]butyl]-8-azaspiro[4.5]decane-7,9-dione hydrochloride, m.p. 219°-220° C.

Anal. Calcd. for $C_{24}H_{32}N_4O_2S.HCl$: C, 60.43; H, 6.98; N, 11.75. Found: C, 60.57; H, 6.98; N, 11.75.

NMR (DMSO-d$_6$): 1.55 (12H, m); 2.64 (4H, s); 3.40 (10H, m); 4.05 (2H, d, 12.0 Hz); 7.50 (2H, m); 8.10 (2H, m); 12.15 (1H, bs).

A sample of the free base product crystallized from acetonitrile containing ethanolic hydrogen chloride affords 8-[4-[4-(1,2-benzisothiazol-3-yl)-1-piperazinyl]butyl]-8-azaspiro[4.5]decane-7,9-dione dihydrochloride dihydrate, m.p. 118°-120° C.

Anal. Calcd. for $C_{24}H_{32}N_4O_2S.2HCl.2H_2O$: C, 52.45; H, 6.97; N, 10.20. Found: C, 52.68; H, 6.91; N, 10.29.

NMR (DMSO-d$_6$): 1.55 (12H, m); 2.64 (4H, s); 3.14 (4H, m); 3.58 (6H, m); 4.06 (2H, d, 12.0 Hz); 5.48 (4H, s); 7.50 (2H, m); 8.10 (2H, m); 11.60 (1H, bs).

Method B. A mixture of 3-(1-piperazinyl)-1,2-benzisothiazole (5.0 g., 0.0228 mole), 1,4-dibromobutane (9.8 g., 0.0456 mole) and finely powdered anhydrous potassium carbonate (7.9 g., 0.057 mole) in 100 ml. of ethanol is stirred and refluxed for a 16 hr. period. The cooled reaction mixture is filtered and the filtrate concentrated in vacuo. Residual solid heated to reflux with 70 ml. of isopropanol and filtered. Concentration of the filtrate to about one-half volume and refrigeration affords 5.58 g. (69.1% yield) of 8-(1,2-benzoisothiazol-3-yl)-8-aza-5-azoniaspiro[4.5]decane bromide, m.p. 246.5°-253° C.

Anal. Calcd. for $C_{15}H_{20}BrN_3S.\frac{1}{4}H_2O$: C, 50.21; H, 5.76; N, 11.71; H$_2$O, 1.26. Found: C, 50.04; H, 5.68; N, 11.60; H$_2$O, 1.50.

A mixture of 3,3-tetramethyleneglutarimide (2.52 g., 0.0151 mole), 8-(1,2-benzisothiazol-3-yl)-8-aza-5-azoniaspir[4.5]decane bromide (5.34 g., 0.0151 mole), powdered potassium carbonate (2.4 g., 0.0173 mole) in 125 ml. of toluene is refluxed and stirred for a 24 hr. period, filtered and evaporated to dryness. Residual material is taken up in boiling toluene and diluted with hot heptane. The hot solution is treated with activated charcoal, filtered and cooled to afford 4.46 g. (67.2% yield) of solid, m.p. 109.5°-120° C. Crystallization from methanol affords 8-[4-[4-(1,2-benzisothiazol-3-yl)-1-piperazinyl]butyl]-8-azaspiro[4.5]decane-7,9-dione free base, m.p. 127.5°-130° C.

EXAMPLE 4

8-[4-[4-(1,2-Benzisoxazol-3-yl)-1-piperazinyl]butyl]-8-azaspiro[4.5]decane-7,9-dione

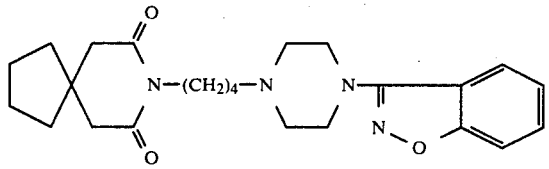

Reaction of 8-(4-bromobutyl)-8-azaspiro[4.5]decane-7,9-dione and 3-(1-piperazinyl)-1,2-benzisoxazole according to the procedure of Example 3 and crystallization of the free base from isopropanol affords a 40% yield of 8-[4-[4-(1,2-benzisoxazol-3-yl)-1-piperazinyl]butyl]-8-azaspiro[4.5]decane-7,9-dione hemihydrate, m.p. 96°-98° C.

Anal. Calcd. for $C_{24}H_{32}N_4O_3 \cdot \frac{1}{2}H_2O$: C, 66.49; H, 7.68; N, 12.93; $H_2O$, 2.08. Found: C, 66.59; H, 7.59; N, 12.87; $H_2O$, 2.38.

NMR (CDCl$_3$): 1.55 (12H, m); 2.41 (2H, m); 2.57 (4H, s); 2.60 (4H, m); 3.57 (4H, m); 3.89 (2H, m); 7.15 (1H, m); 7.41 (2H, m); 7.66 (1H, d, 8.0 Hz).

EXAMPLE 5

3-[4-[4-(1,2-Benzisothiazol-3-yl)-1-piperazinyl]butyl]-2,4-thiazolidinedione

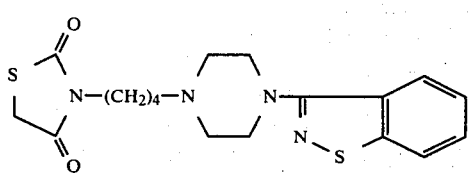

(a) 2,4-Thiazolidinedione sodium salt. 2,4-Thiazolidinedione (11.71 g., 0.1 mole) and 100 ml. of 0.1 N sodium hydroxide (0.1 mole) are mixed and warmed as necessary to effect solution. Concentration of the basic solution under reduced pressure affords a semisolid which, with repeated acetone trituration and removal of solvent in vacuo, provides a crystalline solid. This material is collected, washed with acetone, and dried at 60° C. in vacuo to provide 15.1 g. (95% yield) of the sodium salt of 2,4-thiazolidinedione, m.p. 225° C. (dec.).

(b) 3-(4-Bromobutyl)-2,4-thiazolidinedione. The 2,4-thiazolidinedione sodium salt (13.91 g., 0.1 mole) is added to a solution of 1,4-dibromobutane (64.77 g., 0.3 mole) in 500 ml. of dry dimethylformamide. After stirring the mixture at room temperature for a 16 hr. period, the resulting clear solution is concentrated in vacuo and residual material dissolved in chloroform, filtered, and concentrated in vacuo to an amber oil. Distillation of the oil affords 20.62 g. (81% yield) of 3-(4-bromobutyl)-2,4-thiazolidinedione, b.p. 105°-115° C. at 0.02 mmHg.

(c) 3-[4-[4-(1,2-Benzisothiazol-3-yl)-1-piperazinyl]butyl]-2,4-thiazolidinedione Dihydrochloride. Reaction of 3-(4-bromobutyl)-2,4-thiazolidinedione with 3-(1-piperazinyl)-1,2-benzisothiazole according to the procedure of Example 3 and conversion of the free base to the hydrochloride salt in acetonitrile affords a 45% yield of 3-[4-[4-(1,2-benzoisothiazol-3-yl)-1-piperazinyl]butyl]-2,4-thiazolidinedione dihydrochloride, m.p. 200°-202° C., from acetonitrile.

Anal. Calcd. for $C_{18}H_{22}N_4O_2S_2 \cdot 2HCl$: C, 46.65; H, 5.22; N, 12.09. Found: C, 46.35; H, 5.31; N, 13.10.

NMR (DMSO-d$_6$): 1.70 (4H, m); 3.16 (4H, m); 3.54 (6H, m); 4.06 (2H, d, 12.0 Hz); 4.21 (2H, s); 7.51 (2H, m); 8.10 (2H, m); 11.55 (1H, bs).

EXAMPLE 6

3-[4-[4-(1,2-Benzisoxazol-3-yl)-1-piperazinyl]butyl]-2,4-thiazolidinedione

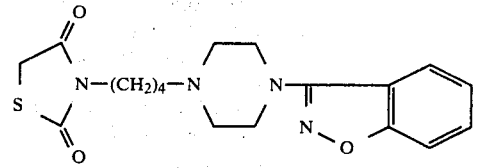

Reaction of 3-(4-bromobutyl)-2,4-thiazolidinedione with 3-(1-piperazinyl)-1,2-benzisoxazole according to the procedure of Example 3 affords a 44% yield of 3-[4-[4-(1,2-benzisoxazol-3-yl)-1-piperazinyl]butyl]-2,4-thiazolidinedione hydrate, m.p. 104.5°-106.6° C., from methanol.

Anal. Calcd. for $C_{18}H_{22}N_4O_3S \cdot \frac{1}{4}H_2O$: C, 57.06; H, 5.99; N, 14.79; $H_2O$, 1.19. Found: C, 57.17; H, 5.98; N, 14.78; $H_2O$, 1.28.

NMR (CDCl$_3$): 1.64 (4H, m); 2.42 (2H, t, 6.6 Hz); 2.61 (4H, m); 3.58 (6H, m); 3.92 (2H, s); 7.42 (4H, m).

EXAMPLE 7

8-[4-[4-(1,2-Benzisothiazol-3-yl)-1-piperazinyl]butyl]-6-thia-8-azaspiro[4.4]nonane-7,9-dione

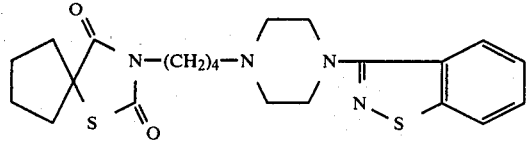

(a) 5-Spirocyclopentyl-2,4-thiazolidindione Sodium Salt. 5-Spirocyclopentyl-2,4-thiazolidindione obtained according to Jones, et al., supra. (1.71 g., 0.01 mole) and 10 ml. of 1.0 N sodium hydroxide (0.01 mole) are mixed and warmed as necessary to effect solution. Concentration of the basic solution with repeated acetone trituration and removal of solvent in vacuo affords 1.66 g. (86% yield) of the sodium salt of 5-spirocyclopentyl-2,4-thiazolidindione, m.p. 243°-245° C.

(b) 3-(4-Bromobutyl)-5-spirocyclopentyl-2,4-thiazolidindione. 5-Spirocyclopentyl-2,4-thiazolidindione sodium salt (3.83 g., 0.019 mole) in 180 ml. of dimethylformamide is slowly added to 1,4-dibromobutane (12.84 g., 0.059 mole) in 20 ml. of dimethylformamide. The mixture is stirred at room temperature for a 16 hr. period and then concentrated under reduce pressure. Residual material dissolved in chloroform, filtered and the filtrate concentrated and distilled affords 4.96 g. (85% yield) of 3-(4-bromobutyl)-5-spirocyclopentyl-2,4-thiazolidinedione, b.p. 122°-126° C. at 0.04 mmHg.

(c) Title Product hydrochloride hydrate. Reaction of 3-(4-bromobutyl)-5-spirocyclopentyl-2,4-thiazolidinedione with 3-(1-piperazinyl)-1,2-benzisothiazole and conversion of the free base to the hydrochloride salt according to the procedure of Example 3 affords an 84% yield of 8-[4-[4-(1,2-benzisothiazol-3-yl)-1-piperazinyl]-butyl]-6-thia-8-azaspiro[4.4]nonane-7,9-dione hydrochloride hydrate, m.p. 214° C., from ethanol.

Anal. Calcd. for $C_{22}H_{28}N_4O_2S_2 \cdot HCl \cdot 0.1\ H_2O$: C, 54.72; H, 6.10; N, 11.60; $H_2O$, 0.37. Found: C, 54.40; H, 6.22; N, 11.40; $H_2O$, 0.46.

NMR (DMSO-$d_6$): 1.74 (8H, m); 2.20 (4H, m); 3.15 (4H, m); 3.52 (6H, m); 4.05 (2H, d, 12.0 Hz); 7.49 (2H, m); 8.09 (2H, m); 11.60 (1H, bs).

EXAMPLE 8

8-[4-[4-(1,2-Benzisoxazol-3-yl)-1-piperazinyl]butyl]-6-thia-8-azaspiro[4.4]nonane-7,9-dione

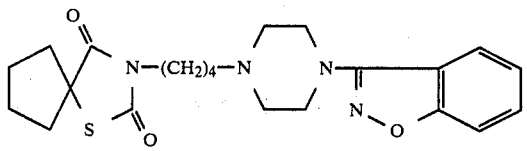

Reaction of 3-(4-bromobutyl)-5-spirocyclopentyl-2,4-thiazolidinedione with 3-(1-piperazinyl)-1,2-benzosoxazole and conversion of the free base to the hydrochloride salt according to the procedure of Example 3 affords an 88% yield of 8-[4-[4-(1,2-benzoisoxazol-3-yl)-1-piperazinyl]butyl]-6-thia-8-azaspiro[4.4]nonane-7,9-dione hydrochloride hydrate m.p. 212°–214° C., from isopropanol.

Anal. Calcd. for $C_{22}H_{28}N_4O_3S \cdot HCl \cdot 0.75\ H_2O$: C, 55.22; H, 6.42; N, 11.71; $H_2O$, 2.82. Found: C, 54.92; H, 6.23; N, 11.51; $H_2O$, 2.42.

NMR (DMSO-$d_6$): 1.75 (8H, m); 2.18 (4H, m); 3.34 (10H, m); 4.07 (2H, d, 12.0 Hz); 7.44 (3H, m); 7.98 (1H, m); 11.20 (1H, bs).

EXAMPLE 9

1-[4-[4-(1,2-Benzisothiazol-3-yl)-1-piperazinyl]butyl]-4-methyl-4-propyl-2,6-piperidinedione

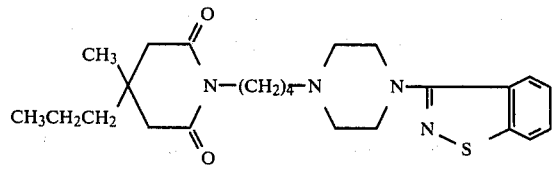

(a) N-(4-(Bromobutyl)-3-methyl-3-n-propylglutarimide. A mixture of 3-methyl-3-n-propylglutarimide (25 g., 0.15 mole) obtained according to N. S. Benica, et al., supra, 1,4-dibromobutane (33.5 g., 0.15 mole), and potassium carbonate (4.6 g., 0.29 mole) is stirred and refluxed for a period of 16 hr. in 250 ml. acetonitrile. Insolubles are removed by filtration and the filtrate concentrated to an oil in vacuo. Distillation of residual oil affords 42.5 g. (95%) of N-(4-bromobutyl)-3-methyl-3-n-propylglutarimide as a light yellow oil, b.p. 165°–190° at 0.09 mm.

(b) Title product hydrochloride. Reaction of N-(4-bromobutyl)-3-methyl-3-n-propylglutarimide with 3-(1-piperazinyl)-1,2-benzisothiazole and conversion of the free base to the hydrochloride salt according to the procedure of Example 3 affords 1-[4-[4-(1,2-benzisothiazol-3-yl)-1-piperazinyl]butyl]-4-methyl-4-propyl-2,6-piperidinedione hydrochloride, m.p. 163°–165° C.

Anal. Calcd. for $C_{24}H_{34}N_4O_2S \cdot HCl$: C, 60.18; H, 7.37; N, 11.70. Found: C, 60.13; H, 7.46; N, 11.52.

NMR (CDCl$_3$): 0.91 (3H, t, 6.0 Hz); 1.01 (3H, s); 1.29 (2H, m); 1.68 (2H, q, 6.8 Hz); 1.85 (4H, m); 2.53 (4H, s); 3.25 (6H, m); 3.79 (2H, t, 6.9 Hz); 4.08 (4H, m); 7.41 (2H, m); 7.84 (2H, m); 12.70 (1H, bs).

EXAMPLE 10

1-[4-[4-(1,2-Benzisothiazol-3-yl)-1-piperazinyl]butyl]-4,4-dimethyl-2,6-piperidinedione

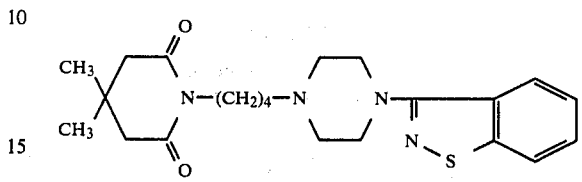

A mixture of N-(4-bromobutyl)-3,3-dimethylglutarimide (4 g., 0.0145 mole) obtained according to the procedure of Example 9, 3-(1-piperazinyl)-1,2-benzisothiazole (3.18 g., 0.0145 mole), anhydrous potassium carbonate (20.04 g., 0.145 mole) and potassium iodide (0.25 g., 0.0015 mole) in 150 ml. of acetonitrile is stirred and refluxed for a period of 12 hr. The reaction mixture is filtered, concentrated in vacuo and residual material triturated with ether. Crystallization of the solid thus obtained from ether affords a 64% yield of analytically pure 1-[4-[4-(1,2-benzisothiazol-3-yl)-1-piperazinyl]butyl]-4,4-dimethyl-2,6-piperidinedione, m.p. 146°–147° C.

Anal. Calcd. for $C_{22}H_{30}N_4O_2S$: C, 63.74; H, 7.29; N, 13.52. Found: C, 63.78; H, 7.11; N, 13.71.

NMR (CDCl$_3$): 1.06 (6H, s); 1.56 (4H, m); 2.48 (4H, s); 2.60 (6H, m); 3.55 (4H, m); 3.80 (2H, t, 7.0 Hz); 7.38 (2H, m); 7.85 (2H, m).

EXAMPLE 11

1-[4-[4-(1,2-Benzisothiazol-3-yl)-1-piperazinyl]butyl]-4,4-diethyl-2,6-piperidinedione

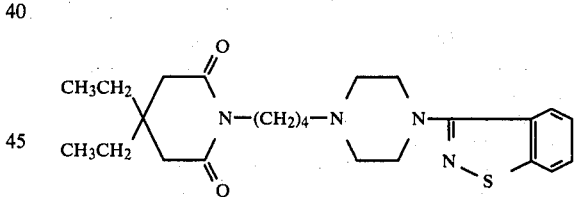

(a) N-(4-Bromobutyl)-3,3-diethylglutarimide. A solution of 3,3-diethylglutarimide (7.0 g., 0.041 mole) obtained according to the procedure of N. S. Benica, et al., supra., and sodium hydroxide (1.64 g., 0.041 mole) in 100 ml. of 70% ethanol is warmed and stirred for a 20 min. period. Concentration of the mixture in vacuo provides the solid sodium salt of 3,3-diethylglutarimide which is suspended in 150 ml. of dimethylformamide and treated with 1,4-dibromobutane (17.7 g., 0.082 mole). The resulting mixture is stirred at room temperature for a period of 48 hr. and then concentrated in vacuo. Residual material dissolved in chloroform, filtered, and the filtrate concentrated and distilled affords 11.4 g. (93% yield) of N-(4-bromobutyl)-3,3-diethylglutarimide.

(b) Title product hydrochloride hydrate. Reaction of N-(4-bromobutyl-3,3-diethylglutarimide and 3-(1-piperazinyl)-1,2-benzisothiazole and conversion of the free base to the hydrochloride salt in isopropanol according to the procedure of Example 3 affords 1-[4-[4-

(1,2-benzisothiazol-3-yl)-1-piperazinyl]butyl]-4,4-diethyl-2,6-piperidinedione hydrochloride hydrate, m.p. 179°–183° C., from acetonitrile.

Anal. Calcd. for $C_{24}H_{34}N_4O_2S.HCl.0.25H_2O$: C, 59.61; H, 7.40; N, 11.59. Found: C, 59.50; H, 7.24; N, 11.50.

NMR (DMSO-$d_6$): 0.79 (6H, t, 7.5 Hz); 1.32 (4H, q, 7.5 Hz); 1.60 (4H, m); 2.55 (4H, s); 3.44 (10H, m); 4.07 (2H, m); 7.52 (2H, m); 8.11 (2H, m); 11.78 (1H, bs).

EXAMPLE 12

4-[4-(1,2-Benzisothiazol-3-yl)-1-piperazinyl]-1-(4-fluorophenyl)-1-butanone

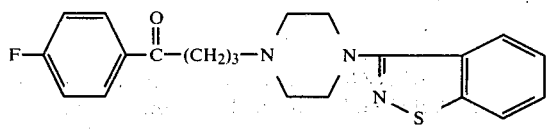

(a) 2-(3-Chloropropyl)-2-(4-fluorophenyl)-1,3-dioxane. As set forth in Chem. Abs. 63, 9959b (1965), a mixture of 4-chloro-4'-fluorobutyrophenone (20 g.), ethylene glycol (6.9 g.) and p-toluensulfonic acid (0.05 g.) in 50 ml. of benzene is refluxed for 30 hr. collecting the water formed. Concentration of the reaction mixture in vacuo affords 2-(3-chloropropyl)-2-(4-fluorophenyl)-1,3-dioxane.

(b) Title product hydrochloride. A mixture of 2-(3-chloropropyl)-2-(4-fluorophenyl)-1,3-dioxane (4.31 g., 0.0176 mole), 3-(1-piperazinyl)-1,2-benzisothiazole (3.86 g., 0.0176 mole), powdered potassium carbonate (2.43 g., 0.0176 mole) and potassium iodide (0.88 g., 0.0053 mole) in 180 ml. of dry acetonitrile is refluxed for a 20 hr. period. The reaction mixture is filtered, concentrated in vacuo and residual oil dissolved in chloroform and filtered. Concentration of the filtrate affords an oily residue which is taken up in 100 ml. of ethanol containing 10 ml. of 3 N hydrochloric acid and refluxed for 15 min. period. Acetonitrile is added to the cooled mixture and the solid obtained collected, 3.3 g. m.p. 248°–250° C. Crystallization of this material from ethanol affords analytically pure 4-[4-(1,2-benzisothiazol-3-yl)-1-piperazinyl]-1-(4-fluorophenyl)-1-butanone hydrochloride, m.p. 251°–254° C.

Anal. Calcd. for $C_{21}H_{22}FN_3OS.HCl$: C, 60.06; H, 5.52; N, 10.01. Found: C, 59.70; H, 5.47; N, 9.78.

NMR (DMSO-$d_6$): 2.12 (2H, m); 3.25 (6H, m); 3.56 (4H, m); 4.06 (2H, d, 12.0 Hz); 7.41 (4H, m); 8.08 (4H, m); 11.60 (1H, bs).

EXAMPLE 13

α-[3-[4-(1,2-Benzisothiazol-3-yl)-1-piperazinyl]propyl]-4-fluorobenzenemethanol

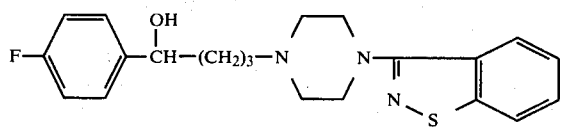

Sodium borohydride (1.0 g., 0.026 mole) is added portionwise to a stirred suspension of 4-[4-(1,2-benzisothiazol-3-yl)-1-piperazinyl]-1-(4-fluorophenyl)-1-butanone hydrochloride (3.34 g., 0.008 mole) in 150 ml. of absolute ethanol. The mixture is stirred for a 20 hr. period, acidified with ethanolic hydrogen chloride, stirred for an additional 2 hr. period and concentrated in vacuo. Residual material is partitioned between chloroform and 1 N aqueous sodium hydroxide and the chloroform phase dried over magnesium sulfate and concentrated in vacuo to afford 2.31 g. (69% yield) of the title compound as the free base. The free base is converted to the hydrochloride in ethanol with ethanolic hydrogen chloride to afford α-[3-[4-(1,2-benzisothiazol-3-yl)-1-piperazinyl]propyl]-4-fluorobenzenemethanol hydrochloride, m.p. 200°–202° C.

Anal. Calcd. for $C_{21}H_{24}FN_3OS.HCl$: C, 59.78; H, 5.97; N, 9.96. Found: C, 59.34; H, 5.95; N, 9.82.

NMR (DMSO-$d_6$): 1.70 (4H, m); 3.40 (8H, m); 4.05 (2H, d, 12.0 Hz); 4.59 (1H, m); 5.30 (1H, bs); 7.35 (6H, m); 8.10 (2H, m); 11.20 (1H, bs).

EXAMPLE 14

4-[4-(1,2-Benzisoxazol-3-yl)-1-piperazinyl]-1-(4-fluorophenyl)-1-butanone

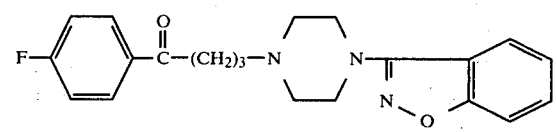

Reaction of 2-(3-chloropropyl)-2-(4-fluorophenyl)-1,3-dioxane with 3-(1-piperazinyl)-1,2-benzisoxazole according to the procedure of Example 12 and conversion of the free base to the hydrochloride salt affords a 25% yield of 4-[4-(1,2-benzisoxazol-3-yl)-1-piperazinyl]-1-(4-fluorophenyl)-1-butanone hydrochloride, m.p. 260°–262°, from methanol (25% yield).

Anal. Calcd. for $C_{21}H_{22}FN_3O_2.HCl$: C, 62.46; H, 5.75; N, 10.41. Found: C, 62.18; H, 5.59; N, 10.50.

NMR (DMSO-$d_6$): 2.11 (2H, m); 2.56 (2H, m); 3.40 (8H, m); 4.12 (2H m); 7.33 (5H, m); 7.60 (1H, m); 8.06 (2H, m); 11.20 (1H, bs).

EXAMPLE 15

α-[3-[4-(1,2-Benzisoxazol-3-yl)-1-piperazinyl]propyl]-4-fluorobenzenemethanol

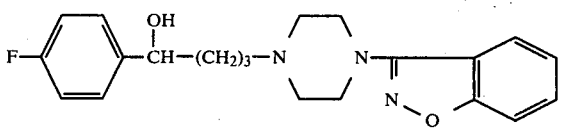

Reduction of 4-[4-(1,2-benzisoxazol-3-yl)-1-piperazinyl]-1-(4-fluorophenyl)-1-butanone hydrochloride (2.0 g., 0.005 mole) with sodium borohydride (0.57 g., 0.015 mole) in 200 ml. of absolute ethanol is carried out according to the procedure of Example 13. Residual material remaining after concentration of the acidified mixture is basified with sodium hydroxide and extracted with chloroform. The combined extracts are dried over magnesium sulfate, concentrated in vacuo and triturated with ether to give 1.2 g. of the free base product. Crystallization of this material from ethanol affords analytically pure α-[3-[4-(1,2-benzisoxazol-3-yl)-1-piperazinyl]propyl]-4-fluorobenzenemethanol, m.p. 142.5°–143.5° C.

Anal. Calcd. for $C_{21}H_{24}FN_3O_2$: C, 68.28; H, 6.55; N, 11.38. Found: C, 68.13; H, 6.56; N, 11.43.

NMR (CDCl$_3$): 1.79 (4H, m); 2.60 (6H, m); 3.64 (4H, m); 4.68 (1H, m); 7.22 (8H, m).

EXAMPLE 16

8-[4-[4-(2,1-Benzisothiazol-3-yl)-1-piperazinyl]butyl]-8-azaspiro[4.5]decane-7,9-dione (a) 3-(1-Piperazinyl)-2,1-benzisothiazole. A mixture of 3-chloro-2,1-benzisothiazole (4.79 g., 0.028 mole obtained according to Albert, et al., J. Het. Chem., 15, 529 (1978) and piperazine (36.2 g., 0.42 mole) is heated for a period of 18 hr. at 120° C. in a closed reactor. The cooled reaction mixture is dissolved in 400 ml. of water and the aqueous solution extracted with ether and then with methylene chloride. The combined extracts are dried over magnesium sulfate and concentrated in vacuo to afford 5.67 (90%) of 3-(1-piperazinyl)-2,1-benzisothiazole free base.

A sample of the free base converted to the hydrochloride salt in ethanol with ethanolic hydrogen chloride affords analytically pure 3-(1-piperazinyl)-2,1-benzisothiazole dihydrochloride, m.p. 274°–276° C. (dec.).

(b) Title product dihydrochloride dihydrate. A mixture of 3-(1-piperazinyl)-2,1-benzisothiazole (4.0 g., 0.018 mole) and 8-(4-bromobutyl)-8-azaspiro[4.5]decane-7,9-dione (5.5 g., 0.018 mole), anhydrous potassium carbonate (4.98 g., 0.036 mole) and potassium iodide (0.83 g., 0.005 mole) in 100 ml. of acetonitrile is stirred at reflux temperature for a period of 20 hr. The reaction mixture is filtered, concentrated in vacuo and residual material triturated with ether to afford 7.38 g., (93% yield) of the title product free base. Conversion of the free base to the hydrochloride salt in ethanol with ethanolic hydrogen chloride and crystallization from ethanol affords 5.34 g. (57% yield) of analytically pure 8-[4-[4-(2,1-benzisothiazol-3-yl)-1-piperazinyl]butyl]-8-azaspiro-[4.5]decane-7,9-dione dihydrochloride hemihydrate, m.p. 225°–227° C. (dec.).

Anal. Calcd. for $C_{24}H_{32}N_4O_2S \cdot 2HCl \cdot 0.5H_2O$: C, 55.17; H, 6.76; N, 10.73. Found: C, 55.55; H, 6.84; N, 10.97.

NMR (DMSO-$d_6$): 1.52 (12H, m); 2.63 (4H, s); 3.57 (12H, m); 7.05 (1H, m); 7.46 (2H, m); 7.90 (1H, d, 8.0 Hz); 9.35 (2H, bs).

EXAMPLE 17

8-[4-[4-(6-Chloro-1,2-benzisoxazol-3-yl)-1-piperazinyl]butyl]-8-azaspiro[4.5]decane-7,9-dione (a) 3-(1-Piperazinyl)-6-chloro-1,2-benzisoxazole. A mixture of 3,6-dichloro-1,2-benzisoxazole and piperazine is reacted according to the procedure of Example 2. The 3-(1-piperazinyl)-6-chloro-1,2-benzisoxazole intermediate is isolated in 79% yield and used without further purification.

(b) Title product. Reaction of 8-(4-bromobutyl)-8-azaspiro[4.5]decane-7,9-dione (2.03 g., 0.067 mole) and 3-(1-piperazinyl)-6-1,2-benzisoxazole (1.6 g., 0.067 mole) according to the procedure of Example 3 provides the crude base which is converted to the hydrochloride salt and crystallized from ethanol. The salt is taken up in water and basified with ammonium hydroxide to provide the free base which crystallized from isopropanol affords 0.3 g. (10% yield) of analytically pure 8-[4-[4-(6-chloro-1,2-benzisoxazol-3-yl)-1-piperazinyl]butyl]-8-azaspiro[4.5]decane-7,9-dione, m.p. 127.5°–128.5° C.

Anal. Calcd. for $C_{24}H_{31}ClN_4O_3$: C, 62.81; H, 6.81; N, 12.21. Found: C, 62.73; H, 6.83; N, 12.35.

NMR (DMSO-$d_6$): 1.48 (12H, m); 2.32 (2H, m); 2.60 (4H, s); 3.40 (10H, m); 7.30 (1H, dd, 8.0, 1.8 Hz); 7.74 (1h, d, 1.8 Hz); 7.98 (1H, d, 8.0 Hz).

What is claimed is:

1. A compound of Formula (I)

wherein R represents the radical wherein
n is 3 or 4,
$R_1$ and $R_2$ are independently lower alkyl of 1 to 4 carbon atoms,
Y is oxygen or sulfur,
Z is hydrogen or halogen
or a pharmaceutically acceptable non-toxic acid addition salt thereof.

2. The compound of claim 1 wherein R is the 8-azaspiro[4.5]decane-7,9-dione radical (a) or a pharmaceutically acceptable acid addition salt thereof.

3. The compound of claim 2 which is 8-[4-[4-(1,2-benzisothiazol-3-yl)-1-piperazinyl]butyl]-8-azaspiro[4.5]-decane-7,9-dione or a pharmaceutically acceptable acid addition salt thereof.

4. The compound of claim 2 which is 8-[4-[4-(1,2-benzisoxazol-3-yl)-1-piperazinyl]butyl]-8-azaspiro[4.5]decane-7,9-dione or a pharmaceutically acceptable acid addition salt thereof.

5. The compound of claim 1 wherein R is the $R_1,R_2$-glutarimide (b) or a pharmaceutically acceptable acid addition salt thereof.

6. The compound of claim 5 which is 1-[4-[4-(1,2-benzisothiazol-3-yl)-1-piperazinyl]butyl]-4-methyl-4-propyl-2,6-piperidinedione or a pharmaceutically acceptable acid addition salt thereof.

7. The compound of claim 5 which is 1-[4-[4-(1,2-benzisothiazol-3-yl)-1-piperazinyl]butyl]-4,4-dimethyl-2,6- piperidinedione or a pharmaceutically acceptable acid addition salt thereof.

8. The compound of claim 5 which is 1-[4-[4-(1,2-benzisothiazol-3-yl)-1-piperazinyl]butyl]-4,4-diethyl-2,6-piperidinedione or a pharmaceutically acceptable acid addition salt thereof.

9. The compound of claim 2 which is 8-[4-[4-(6-chloro-1,2-benzisoxazol-3-yl)-1-piperazinyl]butyl]-8-azaspiro[4.5]decane-7,9-dione or a pharmaceutically acceptable salt thereof.

10. The process for ameliorating a psychotic state in a mammal in need of such treatment which comprises systemic administration to said mammal an effective dose of from about 0.01 to 40 mg/kg body weight of a compound of claim 1.

11. The process of claim 10 in which the compound is 8-[4-[4-(1,2-benzisothiazol-3-yl)-1-piperazinyl]butyl]-8-azaspiro[4.5]decane-7,9-dione.

12. 8-[4-[4-(2,1-Benzisothiazol-3-yl)-1-piperazinyl]butyl]-8-azaspiro[4.5]decane-7,9-dione.

* * * * *